(12) United States Patent
Antoine

(10) Patent No.: US 7,632,260 B2
(45) Date of Patent: Dec. 15, 2009

(54) METHOD FOR PRODUCING A DEVICE FOR CONNECTING A RECEPTACLE AND A CONTAINER, CORRESPONDING CONNECTING DEVICE AND READY-FOR-USE ASSEMBLY COMPRISING A DEVICE OF THIS TYPE

(75) Inventor: Aneas Antoine, Menetrol (FR)

(73) Assignee: Biodome, Issoire (FR)

( * ) Notice: Subject to any disclaimer, the term of this patent is extended or adjusted under 35 U.S.C. 154(b) by 311 days.

(21) Appl. No.: 10/129,208

(22) PCT Filed: Dec. 6, 2000

(86) PCT No.: PCT/FR00/03413

§ 371 (c)(1),
(2), (4) Date: May 3, 2002

(87) PCT Pub. No.: WO01/41699

PCT Pub. Date: Jun. 14, 2001

(65) Prior Publication Data

US 2002/0183714 A1    Dec. 5, 2002

(30) Foreign Application Priority Data

Dec. 10, 1999  (FR) .................... 99 15634

(51) Int. Cl.
    *B65D 39/00* (2006.01)
(52) U.S. Cl. ............ 604/414; 604/403; 604/415; 215/247
(58) Field of Classification Search ............. 604/411, 604/413–416, 403, 905, 533; 215/277, DIG. 3
    See application file for complete search history.

(56) References Cited

U.S. PATENT DOCUMENTS

| 2,847,996 | A | 8/1958 | Cohen et al. |
| 3,902,491 | A | 9/1975 | Lajus |
| 3,976,073 | A | 8/1976 | Quick et al. |
| 4,195,632 | A | 4/1980 | Parker et al. |
| 4,296,786 | A | 10/1981 | Brignola |
| 4,507,113 | A | 3/1985 | Dunlap |
| 4,552,277 | A | 11/1985 | Richardson et al. |

(Continued)

FOREIGN PATENT DOCUMENTS

DE    41 22 476 A1    1/1993

(Continued)

*Primary Examiner*—Leslie R Deak
(74) *Attorney, Agent, or Firm*—K&L Gates LLP

(57) ABSTRACT

According to the inventive method, a first element (22) of the assembly which is formed by the base (8) and the cap (22) of the device, is produced from a harder material than the second element (8) of said assembly (8, 22), the first element (22) is provided with at least one peripheral edge (30) for tightly penetrating an area facing the second element and the/each edge (30) of the first element (8) is/are covered with a lubricating agent which is suitable for forming a lubricating film (26) once the covering process is complete. Said film remains in place on the sealed edge(s), during the relative displacement of the cap (22) and the base (8), as well as when the cap (22) and base (8) are immobile in relation to each other.

This film ensures that the cap can be fairly easily disassembled from the base.

21 Claims, 3 Drawing Sheets

U.S. PATENT DOCUMENTS

| | | | |
|---|---|---|---|
| 4,576,211 A | 3/1986 | Valentini et al. | |
| 4,589,879 A | 5/1986 | Pearson | |
| 4,607,671 A | 8/1986 | Aalto et al. | |
| 4,626,005 A * | 12/1986 | Stifter | 285/124.4 |
| 4,639,250 A | 1/1987 | Rycroft | |
| 4,675,020 A | 6/1987 | McPhee | |
| 4,713,060 A | 12/1987 | Riuli | |
| 4,759,756 A | 7/1988 | Forman et al. | |
| 4,883,483 A | 11/1989 | Lindmayer | |
| 4,898,209 A | 2/1990 | Zbed | |
| 5,152,965 A | 10/1992 | Fisk et al. | |
| 5,169,388 A | 12/1992 | McPhee | |
| 5,186,323 A | 2/1993 | Pfleger | |
| 5,224,515 A | 7/1993 | Foster et al. | |
| 5,232,029 A | 8/1993 | Knox et al. | |
| 5,247,972 A | 9/1993 | Tetrault | |
| 5,279,576 A | 1/1994 | Loo et al. | |
| 5,279,583 A | 1/1994 | Shober, Jr. et al. | |
| 5,308,347 A | 5/1994 | Sunago et al. | |
| 5,342,346 A | 8/1994 | Honda et al. | |
| 5,342,347 A | 8/1994 | Kikuchi et al. | |
| 5,350,372 A | 9/1994 | Ikeda et al. | |
| 5,352,191 A | 10/1994 | Sunago et al. | |
| 5,364,386 A | 11/1994 | Fukuoka et al. | |
| 5,374,264 A | 12/1994 | Wadsworth, Jr. | |
| 5,397,303 A | 3/1995 | Sancoff et al. | |
| 5,423,753 A | 6/1995 | Fowles et al. | |
| 5,423,791 A | 6/1995 | Bartlett | |
| 5,429,256 A | 7/1995 | Kestenbaum | |
| 5,429,614 A | 7/1995 | Fowles et al. | |
| 5,478,337 A | 12/1995 | Okamoto et al. | |
| 5,526,853 A | 6/1996 | McPhee et al. | |
| 5,636,660 A | 6/1997 | Pfleiderer et al. | |
| 5,879,345 A * | 3/1999 | Aneas | 604/411 |
| 6,022,339 A * | 2/2000 | Fowles et al. | 604/411 |
| 6,063,068 A | 5/2000 | Fowles et al. | |
| 6,070,623 A | 6/2000 | Aneas | |
| 6,209,738 B1 * | 4/2001 | Jansen et al. | 215/247 |
| 6,382,442 B1 * | 5/2002 | Thibault et al. | 215/249 |
| 6,681,946 B1 * | 1/2004 | Jansen et al. | 215/249 |

FOREIGN PATENT DOCUMENTS

| | | |
|---|---|---|
| DE | 295 16 650 U1 | 2/1996 |
| EP | 0 458 543 A1 | 11/1991 |
| EP | 0 538 891 A1 | 4/1993 |
| EP | 0 737 485 A1 | 10/1996 |
| EP | 0 728 457 A2 | 11/1996 |
| EP | 0 728 457 A3 | 11/1996 |
| EP | 0 829 250 A2 | 3/1998 |
| EP | 0 829 250 A3 | 3/1998 |
| EP | 0 728 457 B1 | 1/1999 |
| FR | 1423549 | 2/1965 |
| FR | 2753624 A1 | 3/1998 |
| JP | 55-80586 | 11/1978 |
| JP | 64-3188 | 6/1987 |
| JP | 11-171224 | 12/1997 |
| WO | WO 90/03536 A1 | 4/1990 |
| WO | WO 96/00053 A1 | 1/1996 |
| WO | WO 97/10156 A1 | 3/1997 |
| WO | WO 98/13006 A1 | 4/1998 |
| WO | 98/32411 | 7/1998 |
| WO | WO 99/27886 A1 | 6/1999 |
| WO | WO 99/51386 A1 | 10/1999 |

* cited by examiner

METHOD FOR PRODUCING A DEVICE FOR CONNECTING A RECEPTACLE AND A CONTAINER, CORRESPONDING CONNECTING DEVICE AND READY-FOR-USE ASSEMBLY COMPRISING A DEVICE OF THIS TYPE

This Application is a U.S. National filing under § 371 of International Application No. PCT/FR00/03413, filed Dec. 6, 2000, claiming priority from French Appln. No. FR 9915634, filed Dec. 10, 1999 (which is hereby incorporated by reference).

The present invention relates to a process for manufacturing a device for connection between a recipient and a container, to a corresponding connection device and to a ready-to-use assembly comprising such a device.

BACKGROUND OF THE INVENTION

In the medicament-packaging domain, it is known to store a component of a pharmaceutical preparation, such as its active ingredient, in a recipient closed by a stopper made of relatively non-rigid material, such as an elastomer. A liquid can be introduced in this recipient after perforation of the stopper in order to dissolve the component contained in the recipient or place it in suspension, so as to obtain a preparation in liquid form, in particular a medicament or a vaccine, ready to be administered to a patient.

WO-A-97/10156, for example, discloses a device for connection between the afore-mentioned closed recipient and a container. The latter contains liquid capable of being introduced into the recipient, once the latter has been opened by perforation of its stopper. Such a connection device comprises a base adapted to be immobilized on the recipient, in the interior volume of which an inner bore is formed.

This device also comprises a plunger mounted to slide in the afore-mentioned bore, which is provided with a member for perforating the stopper of the recipient, such as a hollow needle. This plunger is mobile between a position of storage, in which the perforation member is not in contact with the stopper, and a position of transfer, in which the perforation member passes through this stopper.

This connection device also comprises a cap comprising a cover from which extend lateral walls defining an opening. This cap is adapted to cover the outer periphery of the base, in particular during storage of the ready-to-use assembly formed by the recipient and its connection device.

In order to avoid any outward microbial migration towards the perforation member, which would contaminate the pharmaceutical preparation intended to come into contact with this member, it is known to provide sealing means between the opposite walls of the base and the cap.

To that end, the teaching of EP-A-0 728 457 provides that the inner wall of the cap presents at least one peripheral edge projecting radially towards the inside. Furthermore, it is provided to coat the outer wall opposite the base by means of a sealing material with high viscosity. During the sliding movement between the base and the cap, the edges of this latter scrape the sealing material disposed on the cap and form a circumferential O-ring, which is possible thanks to the high viscosity of the material used.

However, this known process of manufacture presents certain drawbacks. For example the circumferential seal thus formed does not ensure perfect tightness, whatever the relative pressure conditions between the outside and the inside of the base. In particular, in the case of the pressure prevailing in the inner volume of the base being greater than atmospheric pressure, said circumferential O-ring is capable of being moved away from the edge area, with the result that this seal is in that case no longer able to perform its function of seal satisfactorily.

SUMMARY OF THE INVENTION

In order to overcome these different drawbacks, the invention proposes carrying out a process for manufacturing a connection device which guarantees, on the one hand, a satisfactory seal between the opposite walls of the base and the cap and, on the other hand, an easy dismantling of these two elements.

To that end, it relates to a process for manufacturing a device for connection between a closed recipient and a container, this connection device comprising:

a base intended to be immobilized on this recipient, a plunger mobile in a bore in said base, this plunger being provided with a perforation member adapted to traverse a stopper of the recipient, and a cap covering the outer periphery of the base at least partially, characterized in that a first element of the assembly formed by the base and the cap is made of a material which is harder than the second element of said assembly, in that the first element is provided with at least one peripheral edge intended to penetrate, tightly, in a region of the second element lying opposite, and in that the or each edge of the first element is coated by means of a lubricating agent adapted, once this coating operation is effected, to form a lubricating film adapted to remain in place on the or each sealing edge, during the relative displacement of the cap and the base, and when this cap and this base are immobile with respect to each other.

The invention enables the objects set forth hereinabove to be achieved.

The phase of coating each edge of the hard element by means of a lubricating agent leads to the wetting of these edges and, being given the characteristics of the lubricating agent used, to the formation of a lubricating film which is immobilized on these edges.

The fact of employing at least one sealing edge penetrating in the opposite wall of the element of lesser hardness, leads to the formation of a mechanical barrier preventing any outward microbial propagation towards the inner volume of the base. This guarantees a satisfactory seal for the connection device of the invention.

The difference in hardness between the first and second elements is, on the Shore D scale, between 10 and 15.

Once the cap is mounted on the base, each sealing edge penetrates in the opposite wall of the less hard element to a depth of about 10 to 15 micrometers.

By using a sealing agent whose catching characterististics are such that it leaves a lubricating film fast with the or each element that it coats, an operator is able easily to remove the cap from the base, immediately before use. This film advantageously presents a thickness of between 5 and 10 micrometers. The presence of this film further provides a secondary sealing component, insofar as this film occupies the superficial micro-defects of the element with edges that it coats. Furthermore, being given that it presents a high catching power, this film cannot be driven away as a function of the differences in pressure prevailing between the outside and the inside of the base, which is advantageous over the prior art.

The lubricating agent advantageously presents a viscosity, at 20° C., included between 150 and 1500 centistokes.

The lubricating agent which is used advantageously presents a high spreading power thanks to its low surface tension and its low viscosity. This allows it to fill more satisfactorily the micro-porosities of the edges of the harder element penetrating in the less rigid element The lubricating agent is advantageously non-miscible with water. This hydrophobic nature gives the lubricating film a high power of seal.

The lubricating agent is preferably stable and chemically neutral, and barely subject to evaporation. For example, it presents a factor of evaporation of about 0.5%, determined by a sample of 2 grams of lubricating agent placed in a 50 ml recipient and subjected to a temperature of 150° C. for 24 hours. This lubricating agent advantageously presents a surface tension greater than that of air.

This lubricating agent may be a siliconed oil or a fluorinated oil.

According to another characteristic of the invention, the first element provided with at least one edge is coated by spraying the lubricating agent.

The invention also relates to a device for connection between a closed recipient and a container, this connection device comprising:
a base intended to be immobilized on this recipient,
a plunger mobile in a bore in said base, this plunger being provided with a perforation member adapted to traverse a stopper of the recipient, and
a cap covering the outer periphery of the base at least partially, characterized in that a first element of the assembly formed by the base and the cap is made of a material which is harder than the second element of said assembly, in that the first element is provided with at least one peripheral edge penetrating, tightly, in a region of the second element lying opposite, and in that the or each edge of the first element is coated by means of a lubricating agent adapted to remain in place on the or each edge, during the relative displacement of the cap and the base, and when this cap and this base are immobile with respect to each other.

According to other characteristics of the invention:
the or each edge of the first element penetrates in the opposite wall of the second element, to a depth of between 10 and 15 micrometers.
the lubricating film presents a thickness of between 5 and 10 micrometers; and
the difference in hardness between the first and second elements is included between 10 and 15 on the Shore D scale.

Finally, the invention relates to a ready-to-use assembly comprising a closed recipient containing a product, in particular a pharmaceutical preparation, and a connection device as defined hereinabove, mounted on said recipient.

BRIEF DESCRIPTION OF THE DRAWINGS

The invention will be more readily understood on reading the following description given solely by way of non-limiting example, and with reference to the accompanying drawings in which.

DETAILED DESCRIPTION

Figure 1:
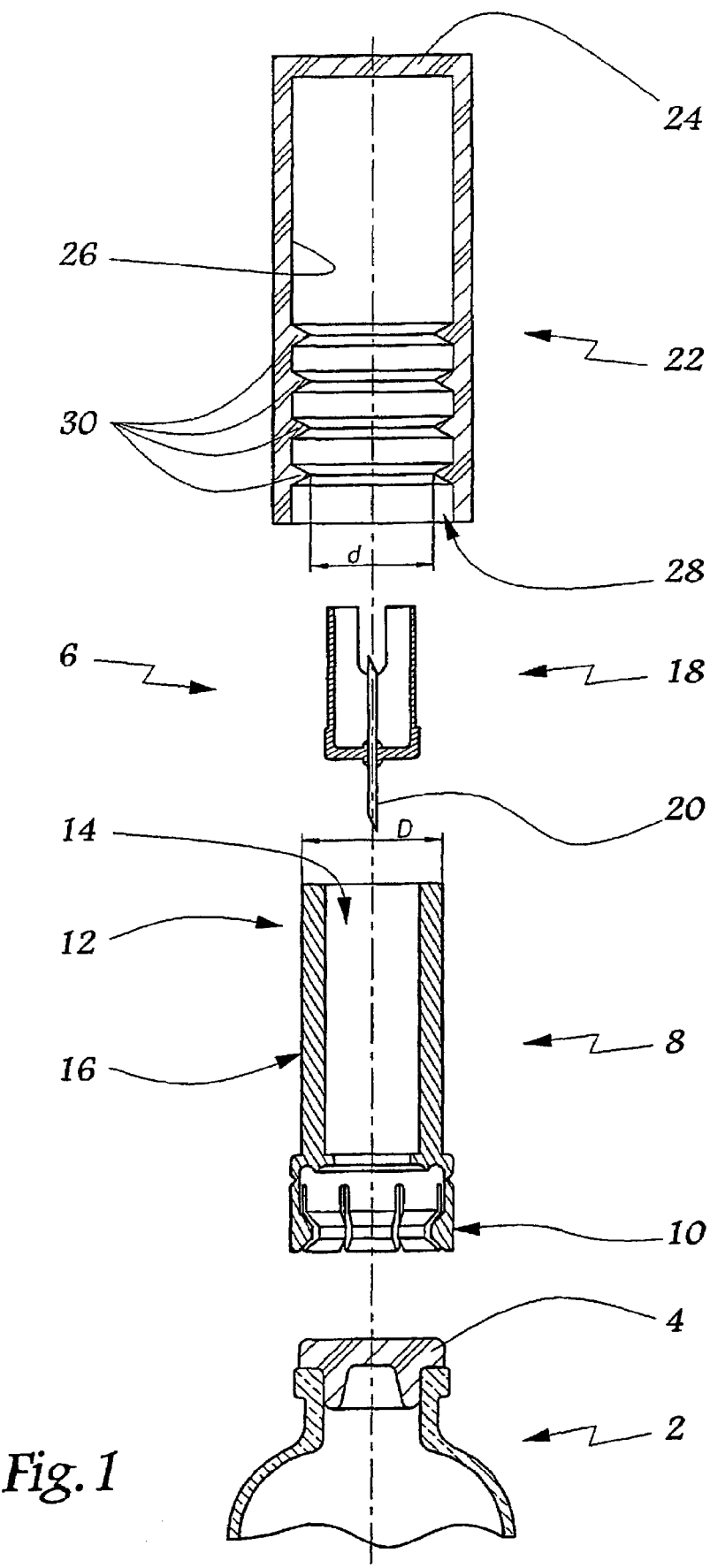
FIG. 1 is a view in longitudinal section illustrating the different elements constituting a connection device according to the invention.

FIG. 1 shows a recipient 2, for example a glass flask, containing a product (not shown) which is, for example, a powder intended to form an oral vaccine. This may equally well be any other type of pharmaceutical preparation, in particular any type of medicaments. The recipient 2 is obturated by means of a stopper 4, made in known manner of a relatively non-rigid material, such as an elastomer.

FIG. 1 also illustrates a device, generally denoted by reference 6, allowing the connection between the recipient 2 and a container (not shown). The latter may be a syringe containing a liquid intended to dissolve the product contained in the recipient 2 or place it in suspension, or a supple bag, or another glass flask.

This connection device 6 comprises a base 8 adapted to be connected on the recipient 2 in known manner by its lower end 10. The latter is extended by a principal cylindrical portion 12 defining an inner bore 14 and a substantially smooth outer peripheral wall 16. The base 8 is made of a relatively non-rigid material such as low density polyethylene.

The connection device 6 also comprises a plunger 18 adapted to slide in the bore 14 of the base 8. This plunger is provided, in known manner, with a needle 20 for perforating the stopper 4. The plunger 18 is mobile between a position of storage, in which the needle is not in contact with the stopper, and a position of transfer, in which the needle 10 transpierces the stopper 4 and is in contact with the liquid contained in the recipient 2.

The connection device of the invention also comprsies a cap, generally denoted by reference 22, which comprises a cover 24 from which extend lateral walls 26, of circular cross-section. These latter define an open end 28 of the cap, intended for fit of the base 8.

The inner periphery of the lateral walls 26 is provided with a plurality of teeth, or edges 30, extending peripherally, radially towards the inside. The cap 22 is made of a material harder than the base 8, for example high density polyethylene.

The edges 30, which have been shown exaggeratedly large in the Figures in order to render the drawings clearer, present an inner diameter d which is smaller than the outer diameter D of the base 8.

Figure 2:
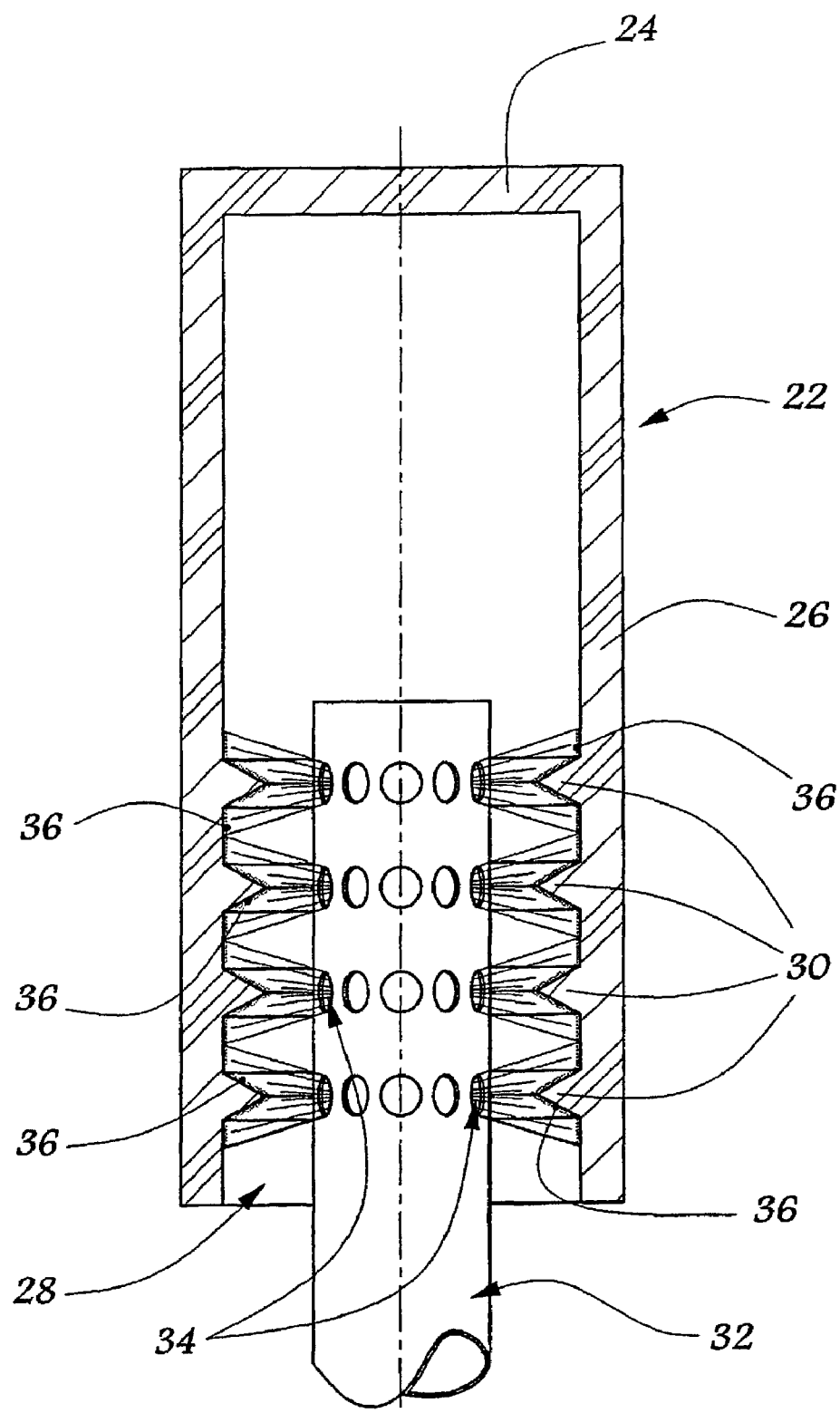
FIG. 2 is a view in longitudinal section illustrating an operation of spraying a lubricating agent forming part of the process of treatment of the invention.

FIG. 2 illustrates a phase of treatment forming part of the process of manufacture of the connection device 6 according to the invention. To that end, a spray device 32 of tubular shape is introduced in the internal volume of the cap 22. Said spray device comprises a plurality of radial orifices 34 ensuring spray of a lubricating agent with which the spray device 32 is supplied.

This lubricating agent is for example a fluorinated oil, such as the one marketed by WYNN'S FRANCE under reference WYNNOX H4, whose viscosity is 180 centistokes at 20° C. A siliconed oil may also be used, such as the one marketed by RHONE POULENC under reference SILBIONE 70 047 V1000, with a viscosity at 25° C. of 1000 centistokes and a surface tension of 21.2 mN/m.

By spraying this lubricating agent on the area of the edges 30, a film 36 is formed on these edges 30, coating them and the vicinity thereof. Being given that the agent used presents a good capacity of catching on the surfaces that it coats, the film 36 presents an excellent holding. This film 36 thus remains fast with the edges 30 that it coats, both in storage position, when the cap 22 and the base 8 are mutually immobilized, and in position of use, when the cap 22 is displaced with respect to the base 8.

Figure 3:
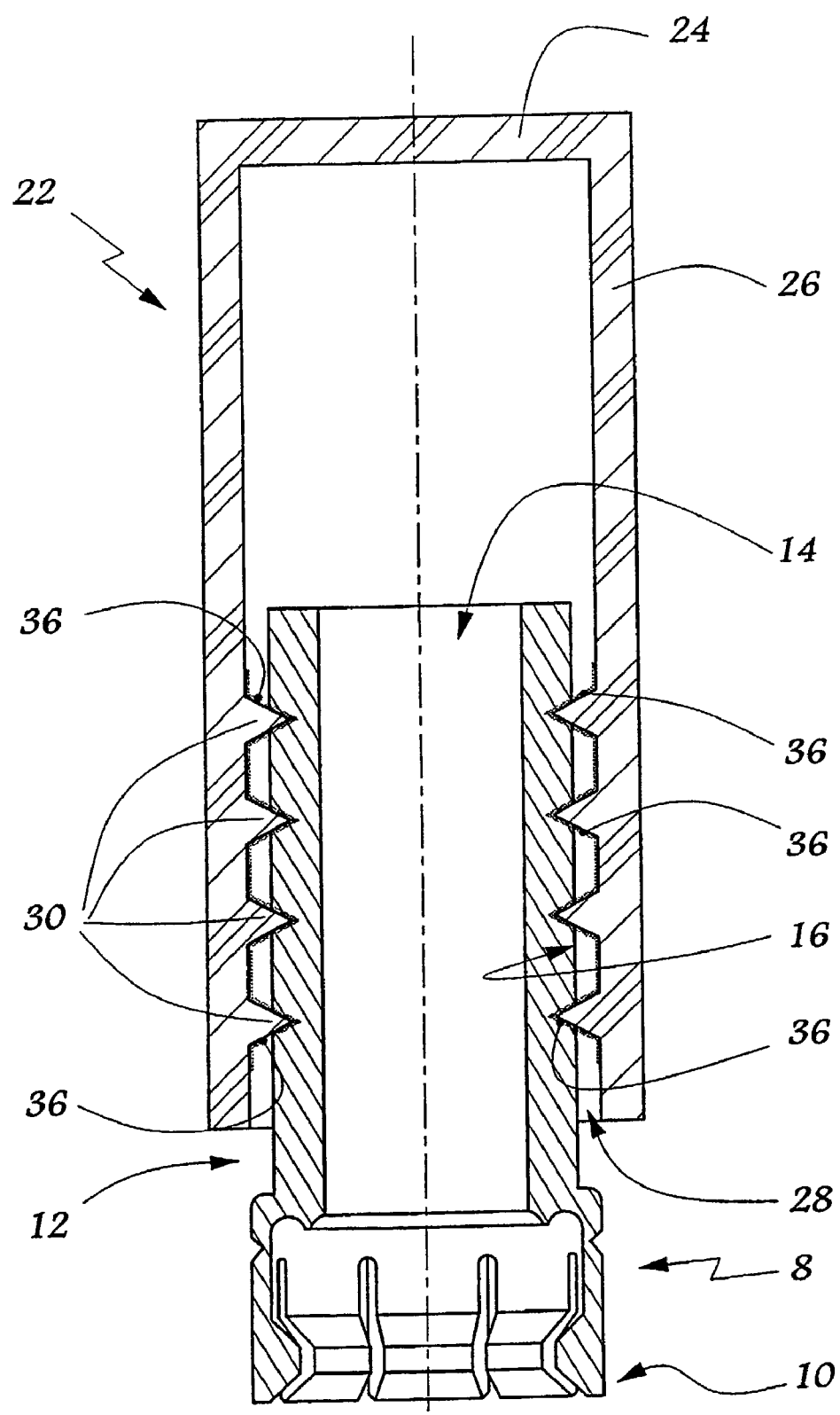
FIG. 3 is a view in longitudinal section, illustrating a base and a cap of the device of FIG. 1, made according to the invention.

FIG. 3 shows a phase of positioning of the connection device 6 of the invention. The plunger 18 (not shown in this FIG. 3) is firstly inserted, in known manner, in the bore 14 of the base 8. Then the cap 22 is added, for example in automatized manner, on the outer periphery of the base 8. The assembly thus constituted is then joined to the recipient 2, so as to be stored. During this phase of storage, the edges 30 penetrate in the opposite wall 16 of the base 8, which provided a satisfactory seal and avoids any outward microbial migration towards the inner volume of the base 8, and therefore of the needle 20. The presence of the film 36 provides a secondary component of seal.

Immediately before use of the connection device 6, the cap 22 is removed from the base 8 by a substantially vertical, upwardly directed action. This action is particularly easy, due to the presence of the film 36 ensuring lubrication between the opposite walls of the cap 22 and the base 8. The stopper 4 of the recipient 2 is then conventionally perforated by means of the needle 20. Finally, the container to which the recipient 2 is to be connected is brought towards the base 8.

The invention is not limited to the examples described and shown. For example, it may be provided to make any number of edges similar to those 30 of the cap 22. Furthermore, it is possible for the base 8 to be made of a harder material than the one constituting the cap 22. In this latter case, the outer periphery of the base 8 is provided with edges, similar to those 30, projecting radially outwardly and cooperating with the smooth inner wall of the cap, said smooth wall presenting an inner diameter smaller than the outer diameter of the edges of the base.

The invention claimed is:

1. A connection device for connection between a closed recipient containing a pharmaceutical preparation and having a stopper and a container, the connection device comprising:
   a base configured to be connected to the recipient and having a bore and an outer periphery;
   a lubricating agent applied to the base;
   a plunger mobile in the bore, the plunger having a perforation member adapted to traverse the stopper; and
   a cap at least partially covering the outer periphery of the base,
   wherein the base and the cap form an assembly having a first element and a second element, the first element being made of a material that is harder than that of the second element, wherein the first element forms a peripheral seal with the second element when edges of the first element penetrate into the second element and the lubricating agent helps to form the peripheral seal.

2. The device of claim 1, wherein the first element penetrates into the second element between 10 and 15 micrometers.

3. The device of claim 1, wherein the lubricating agent has a thickness of between 5 and 10 micrometers.

4. The device of claim 1, wherein the connection device is manufactured as a ready-to-use assembly with a pharmaceutical preparation.

5. The device of claim 1, wherein at least the cap is assembled to the base in an automated manner.

6. The device of claim 1, wherein the plunger, the base and the cap are assembled to the closed recipient in an automated and sterile manner.

7. A ready-to-use assembly comprising a closed recipient having a stopper and containing a pharmaceutical preparation, and a connection device mounted on the recipient, the connection device comprising:
   a base intended to be immobilized on the recipient having a bore and an outer periphery;
   a plunger being mobile in the bore and having a perforation member adapted to a traverse stopper;
   a cap at least partially covering the outer periphery of the base; and
   a lubricating agent applied to at least one of the base and the cap,
   wherein the base and cap form an assembly having a first element and a second element, the first element being made of a material that is harder than that of the second element, and wherein the first element forms a first seal when assembled with the second element when the first element penetrates the second element and a second seal formed by the lubricant on at least one of the first element and the second element, wherein the connection device is assembled ready-for-use with the pharmaceutical preparation.

8. The device of claim 7, wherein the plunger, the base and the cap are assembled to the closed recipient in a sterile manner to avoid microbial migration.

9. The device of claim 7, wherein the base, the plunger and the cap are assembled to the closed recipient in a manufacturing facility.

10. A connection device for connection between a closed recipient containing a pharmaceutical preparation having an opening obstructed by a stopper, and a container, the connection device comprising:
    a base intended to be immobilized on the recipient, the base comprising a bore;
    a plunger mobile in the bore, the plunger comprising a perforation member adapted to traverse the stopper; and
    a cap covering an outer periphery of the base, the cap having peripheral edges, wherein the cap is made of a material that is harder than the material of the base, so that the peripheral edges form a first seal when assembled adjacent a region of the base and edges of the cap penetrate into the base and wherein the connection device is assembled with the closed recipient containing the pharmaceutical preparation.

11. The device of claim 10, wherein the base, the plunger and the cap are assembled to the closed recipient in an automated manufacturing facility.

12. The device of claim 10, wherein the peripheral edges penetrate about 10 and 15 micrometers in the base, and further comprising a second seal formed by a coating on the base or the cap.

13. A connection device for connection between a closed recipient containing a pharmaceutical preparation and a container, the connection device comprising:
    a base configured to be connected to the recipient; and
    a cap covering the outer periphery of the base, wherein one of the base and the cap is made of a material which is harder than the material of the other of the base and the cap and comprises a peripheral edge that forms a penetrating seal when assembled adjacent a region of the other of the base and the cap, wherein the base and the cap are configured for assembly to a closed recipient containing the pharmaceutical preparation during manufacture.

14. The connection device of claim 13, wherein the peripheral edge is coated by a lubricating agent.

15. The connection device of claim 14, wherein the lubricating agent forms a film on the peripheral edge having a thickness of between 5 and 10 micrometers.

16. The connection device of claim 13, further comprising a plunger mobile in a bore in the base, the plunger comprising a perforation member configured to traverse a stopper obstructing an opening of the container.

17. The connection device of claim 13, wherein one of the base and the cap penetrate into the other of the base and the cap between 10 and 15 micrometers.

18. The connection device of claim 13, wherein the difference in the hardness between the material of the cap and the material of the base is, on the Shore D scale, between 10 and 15.

19. The connection device of claim 13, wherein the peripheral edges are located on the cap.

20. The connection device of claim 13, wherein the edge of the one of the base and the cap penetrates about 10 and 15 micrometers in a region of the other of the base and the cap.

21. The device of claim 13, wherein the peripheral edge comprises a thread.

* * * * *